United States Patent [19]

Kenndoff et al.

[11] Patent Number: 5,844,013
[45] Date of Patent: Dec. 1, 1998

[54] HYDROPHILIC POLYURETHANE GEL FOAMS, PARTICULARLY FOR TREATING DEEP WOUNDS, WOUND DRESSING BASED ON HYDROPHILIC POLYURETHANE GEL FOAMS AND METHOD OF MANUFACTURE

[75] Inventors: Jochen Kenndoff; Vadim Lenuck, both of Hamburg; Günther Sachau, Quickborn, all of Germany

[73] Assignee: Beiersdorf AG, Hamburg, Germany

[21] Appl. No.: 406,926

[22] PCT Filed: Oct. 1, 1993

[86] PCT No.: PCT/EP93/02686

§ 371 Date: May 30, 1995

§ 102(e) Date: May 30, 1995

[87] PCT Pub. No.: WO94/07935

PCT Pub. Date: Apr. 14, 1994

[30] Foreign Application Priority Data

| Oct. 2, 1992 | [DE] | Germany | 42 33 289.3 |
| Mar. 17, 1993 | [DE] | Germany | 43 08 445.1 |
| Mar. 17, 1993 | [DE] | Germany | 43 08 347.1 |

[51] Int. Cl.⁶ ............... C08J 9/04; C08J 9/12; C08L 75/04; A61F 13/02; A61F 13/15; A61L 15/20; A61L 15/26; A61L 15/58

[52] U.S. Cl. ........... 521/137; 424/445; 428/318.6; 428/319.3; 428/423.3; 521/121; 521/124; 521/126; 521/128; 521/129; 521/130; 521/159; 521/170; 521/174; 523/105; 523/111; 602/46; 604/304; 604/307; 156/78; 156/79; 427/207.1; 427/208.4; 427/373; 427/393.5

[58] Field of Search ............ 521/137, 170, 521/174, 159, 130, 121, 124, 126, 128, 129; 424/445; 602/46; 523/105, 111; 604/304, 307; 428/318.6, 319.3, 423.3; 427/207.1, 208.4, 373, 393.5; 156/78, 79

[56] References Cited

U.S. PATENT DOCUMENTS

| 4,404,296 | 9/1983 | Schäpel | 523/105 |
| 4,466,936 | 8/1984 | Schäpel | 264/225 |
| 4,661,099 | 4/1987 | von Bittera et al. | 604/290 |
| 5,160,328 | 11/1992 | Cartmell et al. | 604/307 |
| 5,336,695 | 8/1994 | Nass et al. | 521/109.1 |
| 5,362,834 | 11/1994 | Schäpel et al. | 528/58 |

FOREIGN PATENT DOCUMENTS 0190814   8/1986   European Pat. Off. .

*Primary Examiner*—Rabon Sergent
*Attorney, Agent, or Firm*—Sprung Kramer Schaefer & Briscoe

[57] ABSTRACT

Hydrophilic polyurethane gel foams are obtainable from a polyurethane gel defined in the description, from a water-absorbing material and from a non-aqueous foaming agent and can be used in medicine, in particular for the management of deep wounds and wound cavities. Wound dressings are obtainable with a polyurethane sheet as backing and a polyurethane gel foam composed of a polyurethane gel defined in the description, of a water-absorbing material and of a non-aqueous foaming agent.

46 Claims, No Drawings

HYDROPHILIC POLYURETHANE GEL FOAMS, PARTICULARLY FOR TREATING DEEP WOUNDS, WOUND DRESSING BASED ON HYDROPHILIC POLYURETHANE GEL FOAMS AND METHOD OF MANUFACTURE

DESCRIPTION

Hydrophilic polyurethane gel foams, in particular for the treatment of deep wounds, wound dressings based on hydrophilic polyurethane gel foams and production processes The present invention relates to polyurethane gel foams, in particular those for medical applications, and to processes for their production.

The present invention furthermore relates to polyurethane gel foams which absorb and bind aqueous liquids for medical applications, and to processes for their production.

The present invention also relates to polyurethane gel foams which are applied to carrier materials and absorb and bind aqueous liquids for medical applications, for example wound dressings such as wound plasters and adhesive plasters, and to processes for their production.

The polyurethane gel foams which, for example, absorb and bind aqueous liquids are also called "hydrogel foams" or "hydroactive gel foams" hereinafter. Instead of "polyurethane gel foams" it is also possible to use the terms "polyurethane foam gels" or "gel foams" and "foam gels".

Hydrogels are macromolecular, natural or synthetic substances which are able, because of a high content of hydrophilic groups, to bind water by absorption. The water-uptake capacity of many hydrogels is a multiple of the intrinsic weight of the anhydrous substance.

Hydrogels are used in a wide variety of forms in medicine. They are particularly suitable for wound management. They are able to protect wounds from drying out, to absorb wound discharge, to act as matrix for active substances of every type and to act as basis for colonization with autologous or heterologous skin cells.

Hydrogels can be used inter alia in the form of foams. Foams for managing cutaneous wounds or surgical wounds are known per se. Polyurethane foams or collagen foams are mainly used for this.

However, the prior art hydrogels have various disadvantages:

because of their hydrophilicity, most of the suitable substances are soluble in water. This is usually unwanted because such products are not dimensionally stable. In addition, such products dissolve in an unwanted manner at the site of use and are then no longer available for the intended purpose.

Other products are distinguished by extensive polymer crosslinking. Although this avoids some of the disadvantages of the said class of substances, the swellability of these substances is substantially impaired or lost.

Self-adhesive gel foams are also known per se. Although these can in general be fixed very well to the skin, they usually have the disadvantage that their water-uptake capacity is greatly impaired.

Hydrophilic foams composed of polyurethane gels are furthermore known. PCT Application WO-88/01878 describes self-adhesive polyurethane foams or polyurethane foam gels which may, inter alia, contain methacrylates as copolymerized units. However, these foam gels are produced by addition of water.

Polyurethane gels based on a polyurethane matrix and high molecular weight polyols are described in EP-B-0 057 839. Self-adhesive sheet-like structures composed of polyurethane gels are disclosed in EP-B-0 147 588. The polyurethane gels disclosed in these last two publications are not foamed. The self-adhesive gels have isocyanate indices of 15 to 70 (EP 147 588).

It is evident from this that the OH functionality is always present in pronounced excess.

EP-B-57839, which relates not to self-adhesive medical adhesive plasters but to gel compositions or mould-making or pouring compositions containing active substances, has already mentioned the foaming of such compositions with air.

The Patent Application EP 0 453 286 describes superabsorbing foam compositions. The foaming is in this case achieved by the presence of water, where appropriate by additional low-boiling organic solvents.

EP 0 196 364 describes hydrophilic polyurethane foams which can be filled with water-absorbing polymers based on a copolymer of acrylic acid and potassium acetate and are intended for medical purposes. The polyurethane is produced on the basis of MDI. The poly-ether used has a minimum functionality of 2 hydroxyl groups, but preferably 2 to 3 hydroxyl groups. The NCO/OH ratio is stoichiometric. This means that variation of the properties is possible to only a very limited extent. In addition, the polyurethane is not in gel form. Foaming can be carried out with compressed air or with other gases which do not react with the isocyanate or with the aid of low-boiling solvents. The mixture of absorber with polyether polyol takes place in the approximate ratio 3:1. The foam has adhesive properties which must be entirely suppressed by aluminized fabric in order to be usable for wound treatment.

It was now the object of the invention to develop hydrogel foams which contain less absorber than in the prior art, do not in principle require an additional anti-stick layer and have a greater flexibility of properties in respect of adhesive and absorption behaviour. In addition, the spreading of extremely thin foam layers is also to be possible. Moreover, the gel foams are intended on the one hand to adhere to the skin, but on the other hand not to stick to the wound surface.

This object is achieved by self-adhesive, hydrophilic polyurethane gel foams which are obtainable from 1. a polyurethane gel which comprises
   (A) 15–62% by weight, preferably 20–57% by weight, particularly preferably 25–47% by weight, based on the total of (A) and (B) of a covalently crosslinked polyurethane as high molecular weight matrix and
   (B) 85–38% by weight, preferably 80–43% by weight, particularly preferably 75–53% by weight, based on the total of (A) and (B), of one or more polyhydroxyl compounds which are bound in the matrix by secondary valence forces and have an average molecular weight between 1000 and 12000, preferably between 1500 and 8000, particularly preferably between 2000 and 6000, and an average OH number between 20 and 112, preferably between 25 and 84, particularly preferably between 28 and 56, as liquid dispersant, the dispersant being essentially free of hydroxyl compounds with a molecular weight below 800, preferably below 1000, particularly preferably below 1500, and, where appropriate,
   (C) 0–100% by weight, based on the total of (A) and (B), of fillers and/or additives,
   and which is obtainable by reacting a mixture of
   a) one or more polyisocyanates
   b) one or more polyhydroxyl compounds with an average molecular weight between 1000 and 12000, and with an average OH number between 20 and 112, c) where appropriate catalysts or accelerators for the reaction between isocyanate groups and hydroxyl groups and, where appropriate, d) fillers and additives known per se from polyurethane chemistry, this mixture being essentially free of hydroxyl compounds with a molecular weight below 800, the average functionality of the polyisocyanates ($F_I$) being between 2 and 4, the average functionality of the polyhydroxyl compound ($F_P$) being between 3 and 6, and the isocyanate index (K) being given by the formula $$K = \frac{300 \pm X}{(F_I \cdot F_P) - 1} + 7$$

in which $X \leq 120$, preferably $X \leq 100$, particularly preferably $X \leq 90$, and the index K has values between 15 and 70, where the stated averages of molecular weight and OH number are to be understood as number averages, 2. a water-absorbing material and
3. an essentially non-aqueous foaming agent.

It was also an object of the invention to develop hydrogel foams which contain less absorber than in the prior art and do not in principle require an additional anti-stick layer, and are suitable for the treatment of deep wounds.

The foam gel ought to have self-adhesive properties by being able to adhere well to itself so that it can be adapted well to the wound or body cavity but, on the other hand, ought not to stick to the wound surface. In addition, it ought to be able very rapidly to bind very large amounts of liquid which are able to be released again, even under pressure, to only a small extent.

This object is achieved by hydrophilic polyurethane gel foams which are obtainable from 1. a polyurethane gel which comprises
   (A) 35–62% by weight, preferably 42–60% by weight, particularly preferably 49–57% by weight, based on the total of (A) and (B) of a covalently crosslinked polyurethane as high molecular weight matrix and
   (B) 65–38% by weight, preferably 58–40% by weight, particularly preferably 51–43% by weight, based on the total of (A) and (B), of one or more polyhydroxyl compounds which are bound in the matrix by secondary valence forces and have an average molecular weight between 1000 and 12000, preferably between 1500 and 8000, particularly preferably between 2000 and 6000, and an average OH number between 20 and 112, preferably between 25 and 84, particularly preferably between 28 and 56, as liquid dispersant, the dispersant being essentially free of hydroxyl compounds with a molecular weight below 800, preferably below 1000, particularly preferably below 1500, and, where appropriate,
   (C) 0–100% by weight, based on the total of (A) and (B), of fillers and/or additives,
   and which is obtainable by reacting a mixture of
   a) one or more polyisocyanates
   b) one or more polyhydroxyl compounds with an average molecular weight between 1000 and 12000, and with an average OH number between 20 and 112,
   c) where appropriate catalysts or accelerators for the reaction between isocyanate groups and hydroxyl groups and, where appropriate,
   d) fillers and additives known per se from polyurethane chemistry, this mixture being essentially free of hydroxyl compounds with a molecular weight below 800, the average functionality of the polyisocyanates ($F_I$) being between 2 and 4, the average functionality of the polyhydroxyl compound ($F_P$) being between 3 and 6, and the isocyanate index (K) being given by the formula $$K = \frac{300 \pm X}{(F_I \cdot F_P) - 1} + 7$$

in which $X \leq 120$, preferably $X \leq 100$, particularly preferably $X \leq 90$, and the index K has values between 15 and 70, where the stated averages of molecular weight and OH number are to be understood as number averages, 2. a water-absorbing material and
3. an essentially non-aqueous foaming agent.

It was furthermore an object of the invention to develop wound dressings such as wound plasters and adhesive plasters with hydrogel foams for wound management which contain less absorber than in the prior art do not in principle require an additional anti-stick layer, and have a greater flexibility of properties in respect of adhesive and absorption behaviour. The foamed material ought to have different self-adhesive properties depending on the area of application, for example to be able to deal better with the requirements of skin types of different sensitivity. No adhesion to the moist wound surface ought to take place. Another aim is to be able to adjust different absorption behaviour in order in this way to be able to deal better with the special requirements of specific wound types. The absorbed liquid should be retained in the wound covering even under gentle pressure. The liquid ought in addition to be absorbed if possible perpendicular to the wound surface and not be distributed in the surface in order to avoid, for example, maceration on sensitive edges of wounds. The intention furthermore was, especially with thin foam layers, to utilize the high flexibility of the self-adhesive foams in order to ensure seating even in problem zones.

This object is achieved by wound dressings which comprise a polyurethane film as backing and, applied thereto, hydrophilic polyurethane gel foams which are obtainable from 1. a polyurethane gel which comprises
   (A) 25–62% by weight, preferably 30–60% by weight, particularly preferably 40–57% by weight, based on the total of (A) and (B) of a covalently crosslinked polyurethane as high molecular weight matrix and
   (B) 75–38% by weight, preferably 70–40% by weight, particularly preferably 60–43% by weight, based on the total of (A) and (B), of one or more polyhydroxyl compounds which are bound in the matrix by secondary valence forces and have an average molecular weight between 1000 and 12000, preferably between 1500 and 8000, particularly preferably between 2000 and 6000, and an average OH number between 20 and 112, preferably between 25 and 84, particularly preferably between 28 and 56, as liquid dispersant, the dispersant being essentially free of hydroxyl compounds with a molecular weight below 800, preferably below 1000, particularly preferably below 1500, and, where appropriate,
   (C) 0–100% by weight, based on the total of (A) and (B), of fillers and/or additives,
   and which is obtainable by reacting a mixture of
   a) one or more polyisocyanates
   b) one or more polyhydroxyl compounds with an average molecular weight between 1000 and 12000, and with an average OH number between 20 and 112, c) where appropriate catalysts or accelerators for the reaction between isocyanate groups and hydroxyl groups and, where appropriate,
d) fillers and additives known per se from polyurethane chemistry, this mixture being essentially free of hydroxyl compounds with a molecular weight below 800, the average functionality of the polyisocyanates ($F_I$) being between 2 and 4, the average functionality of the polyhydroxyl compound ($F_P$) being between 3 and 6, and the isocyanate index (K) being given by the formula $$K = \frac{300 \pm X}{(F_I \cdot F_P) - 1} + 7$$

in which $X \leq 120$, preferably $X \leq 100$, particularly preferably $X \leq 90$, and the index K has values between 15 and 70, where the stated averages of molecular weight and OH number are to be understood as number averages, 2. a water-absorbing material and
3. an essentially non-aqueous foaming agent.

The polyurethane gel foam serves as wound covering. Would dressings according to the invention are also wound plasters and adhesive plasters.

The polyurethane gels according to the invention can be prepared from the starting compounds known from polyurethane chemistry by processes known per se, as described, for example, in DE-A 31 03 499, DE-A 31 03 500 and EP 147 588. However, it is essential that the conditions defined above are complied with in the selection of the gel-forming components because otherwise non-stick elastic gels are obtained in place of self-adhesive gels.

Polyhydroxyl compounds which are preferred according to the invention are polyether polyols as specified in detail in the abovementioned German Published Specifications.

Suitable as polyisocyanate component are both (cyclo) aliphatic and aromatic isocyanates. Preferred (cyclo) aliphatic polyisocyanates are 1,6-hexamethylene diisocyanate and its biurets and trimers, and hydrogenated diphenylmethane diisocyanate ("MDI") types. Preferred aromatic polyisocyanates are those obtained by distillation, such as MDI mixtures from 4,4' and 2,4' isomers or 4,4'-MDI, and toluylene diisocyanate ("TDI") types. The (cyclo) aliphatic and the aromatic isocyanates may also contain more highly functional portions because of modifications, for example biuretization, trimerization or prepolymerization.

The diisocyanates may be chosen in particular for example from the group of unmodified aromatic or aliphatic diisocyanates or else from modified products formed by prepolymerization with amines, polyols or polyether polyols. 4,4'-diisocyanatodiphenylmethane or else modified products formed by polymerization with polyols or polyether polyols are preferred. 4,4'-Diisocyanatodiphenylmethane liquefied by prepolymerization with tripropylene glycol, for example, has proven very beneficial.

Preferably used are one or more polyether polyols obtainable by addition of propylene oxide and, where appropriate, ethylene oxide on to customary starter molecules and as are described, for example, in EP 147 588.

Preferred polyether polyols are compiled in the following table. They were prepared by addition of propylene oxide and, where appropriate, ethylene oxide on to the stated starter molecules in a manner known per se.

| Polyol No. | Propylene oxide % | Ethylene oxide % | Starter molecule | OH number | OH functionality |
|---|---|---|---|---|---|
| 1 | 80 | 20 | PET | 36 | 4 |
| 2 | 100 | — | sorbitol | 46 | 6 |
| 3 | 73 | 27 | sorbitol | 30 | 6 |
| 4 | 45 | 55 | TMP | 56 | 3 |
| 5 | 100 | — | PET | 72 | 4 |
| 6 | 100 | — | TMP | 56 | 3 |
| 7 | 90 | 10 | sorbitol | 83 | 6 |
| 8 | 100 | — | EDA | 61 | 4 |
| 9 | 83 | 17 | TMP | 35 | 3 |
| 10 | 100 | — | PET | 45 | 4 |

PET = pentaerythritol
TMP = trimethylolpropane
EDA = ethylenediamine

Examples of starter molecules for the polyether polyols are pentaerythritol, sorbitol, trimethylolpropane or ethylenediamine.

The catalysts or accelerators are particularly advantageously selected from the group consisting of organic acids, in particular p-toluenesulphonic acid, n-butylphosphonic acid organotin compounds, including their salts with organic and inorganic acids, in particular tin naphthenate, tin benzoate, dibutyltin dioctoate, dibutyltin diacetate, tin (II) ethylhexoate and dibutyltin acetate iron salts of higher fatty acids, in particular iron stearate amines, for example isophoronediamine, methylenedianiline, imidazoles tertiary amines, in particular trialkylamines, the alkyl radicals each advantageously having 2–6 carbon atoms.

The starting components are chosen according to the invention so that in the gel-forming reaction mixture the average NCO functionality is between 2 and 4, the average polyol functionality is between 3 and 6 and the isocyanate index is between 15 and 70, preferably between 18 and 55, particularly preferably between 20 and 45.

The polyurethane gels may, where appropriate, contain additives known per se from polyurethane chemistry, such as, for example, fillers and chopped fibres with an inorganic or organic basis, metal pigments, surface-active substances or liquid extenders such as substances with a boiling point above 150° C.

Examples of organic fillers which may be mentioned are barytes, chalk, gypsum, kieserite, sodium carbonate, titanium dioxide, cerium oxide, silica sand, kaolin, carbon black and hollow microbeads.

Examples of organic fillers which can be used are powders based on polystyrene, polyvinyl chloride, urea-formaldehyde and polyhydrazodicarbonamide. Examples of suitable chopped fibres are glass fibres 0.1–1 mm long or fibres of organic origin such as, for example, polyester or polyamide fibres. Metal powders, such as, for example, iron or copper powder, can likewise also be used in the gel formation. In order to confer the required colour on the gels according to the invention it is possible to use dyes or coloured pigments with an organic or inorganic basis known per se for colouring polyurethanes such as, for example, iron oxide or chromium oxide pigments, or phthalocyanine- or monoazo-based pigments. Examples of surface-active substances which may be mentioned are cellulose powder, active carbon and silica products.

Examples of liquid extenders which can be used are ethyl stearate, hexyl laurate, isopropyl myristate, isopropyl palmitate or dodecylsulphonic esters.

It is furthermore possible also to use as liquid extenders high molecular weight polyols whose hydroxyl groups are etherified, esterified or urethanized, and liquid paraffins and silicone oils.

The content of fillers and extenders in the gel can preferably be up to 50% by weight based on the total weight of the gel.

To modify the adhesive properties of the gels it is possible where appropriate to add up to a content of 10% by weight, based on the weight of the gel composition, of additives of polymeric vinyl compounds, polyacrylates and other copolymers customary in adhesives technology, and also adhesives based on natural substances.

The fillers and additives can also be selected from the customary classes of substances. Particularly advantageous are dyes, pigments, light stabilizers, preservatives, perfumes, substances with antimicrobial activity, other active substances such as, for example, substances with a cooling effect (for example menthol) or those which promote blood flow or generate a sensation of warmth.

Preferred water-absorbing materials are water-absorbing salts, known as superabsorbers, of polyacrylates and copolymers thereof, in particular the sodium or potassium salts. They may be uncrosslinked or crosslinked and are also obtainable as commercial products. Particularly suitable products are those disclosed in DE-A-37 13 601, and superabsorbers of the new generation with only low remaining contents of water which can be dried out and high swelling capacity under pressure.

Preferred products are polymers based on acrylic acid/sodium acrylate with a small amount of crosslinking. Sodium polyacrylates of this type can be obtained as Favor 922-SK (Chemische Fabrik Stockhausen GmbH, Germany).

Further absorbers are likewise suitable, for example carboxymethylcellulose and karaya.

Hydrophilic polyurethane gel foams

The amounts and procedures indicated below are preferred for hydrophilic polyurethane gel foams.

The amount by weight of the water-absorbing material can be up to 1.5 times the amount by weight of the polyhydroxyl compound. The amount by weight of the water-absorbing material is preferably 100 to 2% by weight, advantageously also 20 to 70% by weight, in particular 35 to 60% by weight, based on the weight of the polyhydroxyl compound.

The water-absorbing material is preferably present in finely ground form, especially when thin foam layers are required. The particle size of the water-absorbing materials, that is to say the diameter of the predominant portion of the particles of this material, is preferably below 300 $\mu$m, preferably below 200 $\mu$m, but in particular below 100 $\mu$m. The particle size is particularly preferably 1 to 100 $\mu$m, in particular 1 to 70 $\mu$m.

Non-aqueous foaming agents which can be used are anhydrous or substantially anhydrous, preferably inert gases or low-boiling solvents which are then present in the polyurethane gel foams in finely dispersed form. It is also possible to use mixtures of these foaming agents. Particularly preferred are air, nitrogen or carbon dioxide or mixtures of these gases, but especially nitrogen. Additional foaming by addition of water is unnecessary. Suitable solvents are low-boiling solvents such as esters, ketones, alkanes and chlorinated hydrocarbons, for example alkyl acetates such as ethyl acetate or trichlorofluoromethane, dichlorodifluoromethane, methylene chloride and the blowing gas substitutes.

The degree of foaming can be varied within wide limits by the amounts of foaming agent incorporated. Thus, the density of the foam can be adjusted to values of about 0.15–1.1 g/cm$^3$. This density range is suitable for wound treatment.

All the starting materials used are preferably anhydrous or substantially anhydrous or have a low water content as industrial products. However, water-containing substances in which the water is bound so that it does not react are also suitable.

The foams according to the invention are advantageously obtainable from

| | |
|---|---|
| 20 | 95% by weight of polyhydroxyl compound |
| 1 | 60% by weight of polyisocyanate |
| 5 | 60% by weight of superabsorber |
| 0.0001 | 10% by weight of accelerator | and the non-aqueous foaming agent in an amount which affords densities of 0.15 to 1.1 g/cm$^3$.

The foams according to the invention are preferably obtainable from

| | |
|---|---|
| 50 | 70% by weight of polyhydroxyl compound |
| 2 | 25% by weight of polyisocyanate |
| 5 | 40% by weight of superabsorber |
| 0.001 | 1% by weight of accelerator | and the non-aqueous foaming agent in an amount which affords densities of 0.3 to 1.0 g/cm$^3$.

It its advantageous to choose polyhydroxyl compound: polyisocyanate weight ratios of (5–35):1, in particular about (10–25):1. The pot life as a measure of the processability of these compositions is between 0.5 and 30 minutes.

The polyether polyols used can be, for example, commercial products such as Levagel VP SN 100, and diisocyanates which have proved suitable are commercial products such as Desmodur PF, Desmodur N 100, IPDI and Desmodur W (commercial products of Bayer AG).

An advantageous commercial product for the accelerators, for example the dibutyltin dilaurate, is Desmorapid Z/SN, and for tin(II) ethylhexoate is Desmorapid SO (Bayer AG).

The invention also relates to the process for producing the polyurethane foams according to the invention, which is characterized in that
1. the components (A), (B) and (C) and a), b), c) and d), of the polyurethane gel which are mentioned and defined above under 1.
2. a water-absorbing material and
3. a non-aqueous foaming agent are combined and mixed together and foamed, with gases being introduced, in particular stirred in or beaten in, during the mixing, and introduced solvents bringing about the foaming by evaporation in the composition, for which purpose the composition is heated where appropriate.

The heating preferably takes place in the curing process which follows where appropriate, in particular at temperatures from 20° to 140° C. and with times from 24 hours to a few seconds.

The gels can be produced in a variety of ways, in particular as described in EP 147 588.

For example, the one-shot or the prepolymer process can be used. In the one-shot process, all the components, that is to say polyols, di- and/or polyisocyanates, the catalysts which increase the rate of the isocyanate polyaddition reaction and, where appropriate, fillers and additives and the other components are combined all at once and vigorously mixed together.

In the prepolymer process, two procedures are possible. Either an isocyanate prepolymer is initially prepared by reacting an appropriate part of the amount of polyol with the total amount of isocyanate intended for the gel formation, and then adding to the resulting prepolymer the remaining amount of polyol and, where appropriate, fillers and additives and the other components and mixing vigorously. Or the total amount of polyol intended for the gel formation is reacted with a part of the amount of isocyanate to give a hydroxyl prepolymer and subsequently the remaining amount of isocyanate is admixed.

A procedure which is particularly advantageous according to the invention is a variant of the one-shot process and of the hydroxyl-prepolymer process. In this case, the polyol or polyol mixture, where appropriate the fillers and additives and the other components, the catalyst and two different isocyanates are combined in one shot and vigorously mixed, one diisocyanate being aliphatic in nature. It can be assumed that, owing to the great difference in reactivity of the two diisocyanates, initially a hydroxyl-prepolymer is produced and then reacts within minutes with the other diisocyanate to form a gel.

In these procedures it is possible for the conveyance, metering and mixing and foaming of the individual components and of the other components or component mixtures to take place with equipment known per se to the person skilled in polyurethane chemistry.

Foaming with a non-aqueous foaming agent, preferably by stirring in or beating in air, is known per se but has particular advantages in this specific case: The advantageous polyurethane gels according to the invention can easily be controlled between slightly and very strongly adhesive by altering the NCO/OH ratio. This accurate control is possible in a simple manner only when an essentially anhydrous process is carried out. The reason for this is the extremely high water-absorption capacity of the superabsorbers because added water, which must be available for the foaming process, may be and is removed in the process in an uncontrolled manner, so that it becomes much more difficult to adjust the product properties in a targeted manner.

The foam material according to the invention meets all the specified requirements.

Surprisingly, the gel foams according to the invention show the property that they completely lose adhesive properties in the moist milieu of the wound. In addition, it is easily possible to control different absorption behaviour. By contrast, the foams according to the invention show the required self-adhesive properties on uninjured skin.

In particular, it is possible to control the adhesion properties of the foams according to the invention by the ratio of polyol to isocyanate.

The absorption behaviour is, in particular, improved by foaming and the addition of water-absorbing agents. It is additionally possible in this way to control the absorption rate while the total binding capacity remains the same. For example, when the foaming is greater and/or the superabsorber content is higher there is faster uptake of wound discharge.

The foams can be poured out or spread out to give sheet-like structures after a pot life which is advantageously about 0.5–30 minutes. Foam thicknesses from 0.015 mm to 15 cm can be obtained without difficulty in this way. The use of finely ground absorber makes it possible to produce thin composition applications of up to 15 g/m$^2$ on spreading. However, it is also possible and advantageous to fabricate from the hydrogel foams according to the invention articles which are not sheet-like but markedly space-filling, for example by customary casting processes.

The resulting foams are open-cell foams. It is thus unnecessary to convert them into such by cutting processes.

The hydrogel foams according to the invention can also advantageously be applied by processes known per se to sheet-like backings, for example woven, knitted, nonwoven fabrics or sheets. The invention likewise relates to the resulting products.

The backing materials contained in these self-adhesive sheet-like structures according to the invention may have a wide variety of origins, that is to say materials based on natural, semisynthetic or completely synthetic raw materials, and of organic or inorganic origin can be used. It is possible to use, for example, plastic and metal sheets, mats, nonwoven, knitted or woven fabrics of organic or inorganic fibre material, paper and foam sheets or also combinations of these backing materials. Sheet-like structures which are permeable to air and moisture are preferred for medical use, for example micro- and macroporous plastic sheets and nonwoven fabrics, and elastic textile backing materials, especially stretch fabrics, and gauze bandages. Polyurethane sheets are particularly preferred, especially those described hereinafter.

The invention furthermore relates to a process for the production of self-adhesive sheet-like structures based on backing materials coated with polyurethane gel foams; the process is characterized in that the foams defined above or reaction mixtures able to form foam gels are applied to the surface of a backing material, for example by direct processes or reverse processes by casting or knife application, with the surface being, where appropriate, only partially covered by the gel-forming reaction mixture. The layer thickness of the gel foam can be, for example, between 0.015 mm and 150 mm, preferably between 0.1 mm and 50 mm, particularly preferably between 0.1 mm and 6 mm.

The sheet-like structures according to the invention can be produced continuously or batchwise. The procedure depends on the given sheet-like structures to be provided with an adhesive layer. A batchwise procedure is often advantageous when backing materials which have already been cut out are available. The continuous procedure is advisable for coating backing materials which are available in continuous form, for example as rolled material. The application of the foam adhesive layer to the backing material can in this case take place directly or by the reverse process. The reaction mixture can also be applied by knife in the said processes before it solidifies due to the reaction.

Although the cohesion of the foams according to the invention is good, it may be advantageous subsequently to treat the foams and sheet-structures according to the invention by irradiation with gamma rays, which improves the cohesion in the gel layer.

Although it is, as mentioned, possible to control the adhesion properties of the foams according to the invention so that the resulting foams, or the backings coated therewith, can be satisfactorily self-adhesive, they can advantageously be coated on one of the two or else both large areas with a customary self-adhesive composition.

The invention also relates to the use of the polyurethane gel foams according to the invention or of the self-adhesive sheet-like structures produced therewith in medicine, for example for the treatment of defect wounds or for the prophylaxis thereof, in particular as adhesive plaster or wound dressing or wound plaster, bandage or support, and as protection and padding material, in particular for prophylaxis.

The finished foam, preferably the sheet-like structures described previously, but also advantageously the backings coated with hydrogel foam, can be used, for example, to manage superficial wounds or surgical wounds.

A particularly advantageous application is the management of deep wounds. This is particularly because the foams according to the invention are able to adhere to one another. One or more thin foam layers, which can individually be cut very conveniently into suitable shapes, can, for example, be modelled and adapted to the wound without further fixation aids being necessary. This results in the same effect being achieved as with thick foam layers.

The good cohesive property of the foams according to the invention makes them also very suitable for use on cohesive bandages. For this purpose they are applied, for example, to elastic or rigid backing materials.

Within the scope of the present application, all amounts and percentage data are, unless indicated otherwise, based on the weight and the complete composition of the formulation.

Treatment of deep wounds

Amounts and procedures indicated below are preferred for polyurethane gel foams which are particularly suitable for the treatment of deep wounds.

The amount by weight of the water-absorbing material can be up to 1.5 times the amount by weight of the polyhydroxyl compound. The amount of weight of the water-absorbing material is preferably 5 to 67% by weight, advantageously also 10 to 52% by weight, in particular 15 to 40% by weight, based on the weight of the polyhydroxyl compound.

The water-absorbing material is preferably present in finely ground form. The particle size of the water-absorbing materials, that is to say the diameter of the predominant portion of the particles of this material, is preferably below 300 $\mu$m, preferably below 200 $\mu$m, but in particular below 100 $\mu$m. The particle size is particularly preferably 10 to 70 $\mu$m.

Non-aqueous foaming agents which can be used are anhydrous or substantially anhydrous, preferably inert gases or low-boiling solvents which are then present in the polyurethane gel foams in finely dispersed form. It is also possible to use mixtures of these foaming agents. Particularly preferred are air, nitrogen or carbon dioxide or mixtures of these gases, but especially nitrogen. Additional foaming by addition of water is unnecessary. Suitable solvents are low-boiling solvents such as esters, ketones, alkanes and chlorinated hydrocarbons, for example alkyl acetates such as ethyl acetate or trichlorofluoromethane, dichlorodifluoromethane, methylene chloride and the blowing gas substitutes.

The degree of foaming can be varied within wide limits by the amounts of foaming agent incorporated. First, the density of the foam can be adjusted to values of about 0.15–1.1 g/cm$^3$. This density range is suitable for wound treatment. Densities between 0.30 and 0.65 g/cm$^3$ are preferred, in particular densities between 0.45 and 0.6 g/cm$^3$.

It is not worthwhile to indicate numerical values for the amounts of foaming agent even in wide limits because these always depend directly on the output rate, for example per minute, of material to be foamed, also variations in density of the material to be foamed are included, and solubility and gas-emission phenomena are possible during production, depending on the qualities of the raw materials.

The density should therefore always be adjusted by testing, which can take place within minutes with suitable technical equipment and entails no difficulties for the skilled person.

Depending on the quality of the raw materials used, preferably 4.7–6.9% by weight, preferably 5.0–6.4% by weight, but in particular 5.4–5.9% by weight of isocyanate are added as crosslinker based on the amount by weight of polyhydroxyl compounds used.

The content by weight of polyhydroxyl compound based on the total weight of the raw materials used can be between 60 and 80% by weight, preferably between 63 and 77% by weight, but in particular between 65 and 75% by weight.

The content by weight of superabsorber based on the total weight of the raw materials used can be between 20 and 40, preferably between 23 and 37% by weight, but in particular between 25 and 35% by weight.

All the starting materials used are preferably anhydrous or substantially anhydrous or have a low water content as industrial products. However, water-containing substances in which the water is bound so that it does not react are also suitable.

The foams according to the invention are advantageously obtainable from

| | |
|---|---|
| 40 | 95% by weight of polyhydroxyl compound |
| 1 | 20% by weight of polyisocyanate |
| 1 | 60% by weight of superabsorber |
| 0.0001 | 10% by weight of accelerator | and the non-aqueous foaming agent in an amount which affords densities of 0.15 to 1.1 g/cm$^3$, preferably between 0.3 to 0.65 g/cm$^3$, particularly preferably between 0.45 and 0.60 g/cm$^3$.

Foams according to the invention are preferably obtainable from

| | |
|---|---|
| 55 | 80% by weight of polyhydroxyl compound |
| 2 | 10% by weight of polyisocyanate |
| 20 | 40% by weight of superabsorber |
| 0.001 | 1% by weight of accelerator | and the non-aqueous foaming agent in an amount which affords densities of 0.45 to 0.6 g/cm$^3$.

It its advantageous to choose polyhydroxyl compound: polyisocyanate weight ratios of (10–35):1, in particular about (15–25):1. The pot life as a measure of the processability of these compositions is between 0.5 and 30 minutes.

The polyether polyols used can be, for example, commercial products such as Levagel VP SN 100, and diisocyanates which have proved suitable are commercial products such as Desmodur PF, Desmodur N 100, IPDI and Desmodur W (commercial products of Bayer AG).

An advantageous commercial product for the accelerators, for example the dibutyltin dilaurate, is Desmorapid Z/SN, and for tin(II) ethylhexoate is Desmorapid SO (Bayer AG).

The invention also relates to the process for producing the polyurethane foams according to the invention, which is characterized in that
1. the components (A), (B) and (C) and a), b), c) and d), of the polyurethane gel which are mentioned and defined above under 1.
2. a water-absorbent material and
3. a non-aqueous foaming agent are combined and mixed together and foamed, with gases being introduced, in particular stirred in or beaten in, during the mixing, and introduced solvents bringing about the foaming by evaporation in the composition, for which purpose the composition is heated where appropriate.

The heating preferably takes place in the curing process which follows where appropriate, in particular at temperatures from 20° to 140° C. and with times from 24 hours to a few seconds.

The gels can be produced in a variety of ways, in particular as described in EP 147 588.

For example, the one-shot or the prepolymer process can be used. In the one-shot process, all the components, that is to say polyols, di- and/or polyisocyanates, the catalysts which increase the rate of the isocyanate polyaddition reaction and, where appropriate, fillers and additives and the other components are combined all at once and vigorously mixed together.

In the prepolymer process, two procedures are possible. Either an isocyanate prepolymer is initially prepared by reacting an appropriate part of the amount of polyol with the total amount of isocyanate intended for the gel formation, and then adding to the resulting prepolymer the remaining amount of polyol and, where appropriate, fillers and additives and the other components and mixing vigorously. Or the total amount of polyol intended for the gel formation is reacted with a part of the amount of isocyanate to give a hydroxyl prepolymer and subsequently the remaining amount of isocyanate is admixed.

A procedure which is particularly advantageous according to the invention is a variant of the one-shot process and of the hydroxyl-prepolymer process. In this case, the polyol or polyol mixture, where appropriate the fillers and additives and the other components, the catalyst and two different isocyanates are combined in one shot and vigorously mixed, one diisocyanate being aliphatic in nature. It can be assumed that, owing to the great difference in reactivity of the two diisocyanates, initially a hydroxyl-prepolymer is produced and then reacts within minutes with the other diisocyanate to form a gel.

In these procedures it is possible for the conveyance, metering and mixing and foaming of the individual components and of the other components or component mixtures to take place with equipment known per se to the person skilled in polyurethane chemistry.

Foaming with a non-aqueous foaming agent, preferably by stirring in or beating in air, is known per se but has particular advantages in this specific case:

The advantageous polyurethane gel foams according to the invention can thus easily be adjusted to adhere weakly to the skin and adhere well to itself by altering the ratio of polyhydroxyl compound to isocyanate. A reduction in the added amount of isocyanate, based on the polyhydroxyl compound, increases the adhesive force, and an increase in the added amount of isocyanate reduces the adhesive force. This accurate control is possible in a simple manner only when an essentially anhydrous process is carried out. The reason for this is the extremely high water-absorption capacity of the superabsorbers because added water, which must be available for the foaming process, may be and is removed in the process in an uncontrolled manner, so that it becomes much more difficult to adjust the product properties in a targeted manner.

The foam material according to the invention meets all the specified requirements, and absorbs wound fluid rapidly and reliably.

Surprisingly, the gel foams according to the invention have the property of completely losing in the moist wound milieu adhesive properties for the wound surface. In addition, they show a rapid absorption with high uptake capacity. The foam is moreover weakly adhesive but adheres satisfactorily to itself so that the foam can be modelled appropriately for the wound or the body orifice. The modelling can moreover be reversible and be reshaped several times so that the material can be adapted well to a deep wound, body cavity or body orifice without problems. It is moreover also possible for several parts to be brought together in a stack, overlapping or in another form and adapted to a wound or orifice, irrespective of its nature, which is larger than the individual foam product. They can be removed in one piece from the wound cavity because they remain bonded together during use.

The foams can be poured out or spread out to give sheet-like structures after a pot life which is advantageously about 0.5–30 minutes. Foam thicknesses from 0.015 mm to 15 cm can be obtained without difficulty in this way. Foam thicknesses of 2 to 6 mm have proved advantageous. However, it is also possible and advantageous to fabricate from the hydrogel foams according to the invention articles which are not sheet-like but markedly space-filling, for example by customary casting processes.

The resulting foams are open-cell foams. It is thus unnecessary to convert them into such by cutting processes.

Although the cohesion of the foams according to the invention is good, it may be advantageous to treat the foams and sheet-like structures according to the invention subsequently by irradiation with gamma rays, which improves the cohesion in the gel layer. There is the additional possibility of further increasing the good stability of the foams by foam introduction into completely covered sheet-like structures, such as, for example, nonwoven, woven and knitted fabrics, in elastic or non-elastic form.

The invention also relates to the use of the polyurethane gel foams according to the invention or of the sheet-like structures which are produced therewith and are weakly adhesive and adhere well to themselves in medicine, for example for the treatment of deep wounds, defect wounds and wound cavities. Use in dental medicine is also possible, for example for binding saliva or for drying tooth cavities or for keeping them dry.

The management of deep wounds is particularly favourable because the foams according to the invention are able to adhere to one another. One or more thin layers of foam which can individually be cut very conveniently to suitable shapes can, for example, be modelled and adapted to the wound without requiring further fixation aids. This results in the same effect being achieved as with thick foam layers.

Within the scope of the present application, all amounts and percentage data are, unless indicated otherwise, based on the weight and the complete composition of the formulation.

Wound dressings

The amounts and procedures indicated below are preferred for the polyurethane gel foams which are suitable in particular for wound dressings.

The amount by weight of the water-absorbing material can be, for example, up to 1.5 times the amount by weight of the polyhydroxyl compound. The amount by weight of the water-absorbing material is preferably 2 to 50% by weight, advantageously also 5 to 40% by weight, in particular 10 to 35% by weight, based on the weight of the polyhydroxyl compound.

The water-absorbing material is preferably present in finely ground form, especially when thin foam layers are required. The particle size of the water-absorbing materials, that is to say the diameter of the predominant portion of the particles of this material, is preferably below 300 μm, preferably below 200 μm, but particularly preferably below 100 μm, in particular below 70 μm. The particle size is preferably 1 to 70 μm.

Non-aqueous foaming agents which can be used are anhydrous or substantially anhydrous, preferably inert gases or low-boiling solvents which are then present in the polyurethane gel foams in finely dispersed form. It is also possible to use mixtures of these foaming agents. Particularly preferred are air, nitrogen or carbon dioxide or mixtures of these gases, but especially nitrogen. Additional foaming by addition of water is unnecessary. Suitable solvents are low-boiling solvents such as esters, ketones, alkanes and chlorinated hydrocarbons, for example alkyl acetates such as ethyl acetate or trichlorofluoromethane, dichlorodifluoromethane, methylene chloride and the blowing gas substitutes.

The degree of foaming can be varied within wide limits by the amounts of foaming agent incorporated. Thus, the density of the foam can be adjusted to values of about 0.15–1.1 g/cm$^3$. This density range is suitable for wound treatment. Different densities can be adjusted as required. Thus, for example, it is possible to produce a foam which absorbs aqueous liquids very rapidly. Particularly suitable for this purpose are foam densities from 0.30 to 0.65 g/cm$^3$, but in particular from 0.45 to 0.6 g/cm$^3$ (a).

For a foam product with high absorption capacity but only moderately rapid absorption behaviour, foam densities from 0.6 to 0.9 g/cm$^3$, but in particular from 0.65 to 0.8 g/cm$^3$, are advantageous (b).

For products with slow absorption behaviour with high capacity, very suitable densities are from 0.8 to 1.0 g/cm$^3$, in particular from 0.85 to 0.95 g/cm$^3$ (c).

All the starting materials used are preferably anhydrous or substantially anhydrous or have a low water content as industrial products. However, water-containing substances in which the water is bound so that it does not react are also suitable.

The foams according to the invention are advantageously obtainable from

| | |
|---|---|
| 20 | 95% by weight of polyhydroxyl compound |
| 1 | 30% by weight of polyisocyanate |
| 1 | 60% by weight of superabsorber |
| 0.0001 | 10% by weight of accelerator | and the non-aqueous foaming agent in an amount which affords densities of 0.15 to 1.1 g/cm$^3$, and in particular the densities indicated above, depending on the desired absorption behaviour.

The foams according to the invention are therefore preferably obtainable from

| | |
|---|---|
| 55 | 85% by weight of polyhydroxyl compound |
| 2 | 15% by weight of polyisocyanate |
| 5 | 40% by weight of superabsorber |
| 0.001 | 1% by weight of accelerator | and the non-aqueous foaming agent in an amount such that
(a) densities from 0.30 to 0.65 g/cm$^3$, but in particular 0.45 to 0.6 g/cm$^3$, or
(b) densities from 0.6 to 0.9 g/cm$^3$, but in particular 0.65 to 0.8 g/cm$^3$, or
(c) densities from 0.8 to 1.0 g/cm$^3$, but in particular 0.85 to 0.95 g/cm$^3$, are obtained.

These density ranges correspond to the properties indicated above under (a)–(c).

It is not worthwhile to indicate numerical values for the amounts of foaming agent even in wide limits because these always depend directly on the output rate, for example per minute, of material to be foamed, also variations in density of the material to be foamed are included, and solubility and gas-emission phenomena are possible during production, depending on the qualities of the raw materials.

The density should therefore always be adjusted by testing, which can take place within minutes with suitable technical equipment and entails no difficulties for the skilled person.

It is advantageous to choose polyhydroxyl compound:polyisocyanate weight ratios of (5–35):1, in particular about (10–25):1. The pot life as a measure of the processability of these compositions is between 0.5 and 30 minutes.

The polyether polyols used can be, for example, commercial products such as Levagel VP SN 100, and diisocyanates which have proved suitable are commercial products such as Desmodur PF, Desmodur N 100, IPDI and Desmodur W (commercial products of Bayer AG).

An advantageous commercial product for the accelerators, for example the dibutyltin dilaurate, is Desmorapid Z/SN, and for tin(II) ethylhexoate is Desmorapid SO (Bayer AG).

The invention also relates to the process for producing the polyurethane foams according to the invention, which is characterized in that
1. the components (A), (B) and (C) and a), b), c) and d), of the polyurethane gel which are mentioned and defined above under 1.
2. a water-absorbing material and
3. a non-aqueous foaming agent
are combined and mixed together and foamed, with gases being introduced, in particular stirred in or beaten in, during the mixing, and introduced solvents bringing about the foaming by evaporation in the composition, for which purpose the composition is heated where appropriate.

The heating preferably takes place in the curing process which follows where appropriate, in particular at temperatures from 20° to 140° C. and with times from 24 hours to a few seconds.

The gels can be produced in a variety of ways, in particular as described in EP 147 588.

For example, the one-shot or the prepolymer process can be used. In the one-shot process, all the components, that is to say polyols, di- and/or polyisocyanates, the catalysts which increase the rate of the isocyanate polyaddition reaction and, where appropriate, fillers and additives and the other components are combined all at once and vigorously mixed together.

In the prepolymer process, two procedures are possible. Either an isocyanate prepolymer is initially prepared by reacting an appropriate part of the amount of polyol with the total amount of isocyanate intended for the gel formation, and then adding to the resulting prepolymer the remaining amount of polyol and, where appropriate, fillers and additives and the other components and mixing vigorously. Or the total amount of polyol intended for the gel formation is reacted with a part of the amount of isocyanate to give a hydroxyl prepolymer and subsequently the remaining amount of isocyanate is admixed.

A procedure which is particularly advantageous according to the invention is a variant of the one-shot process and of the hydroxyl-prepolymer process. In this case, the polyol or polyol mixture, where appropriate the fillers and additives and the other components, the catalyst and two different diisocyanates are combined in one shot and vigorously mixed, one diisocyanate being aliphatic in nature. It can be assumed that, owing to the great difference in reactivity of the two diisocyanates, initially a hydroxyl-prepolymer is produced and then reacts within minutes with the other diisocyanate to form a gel.

In these procedures it is possible for the conveyance, metering and mixing and foaming of the individual components and of the other components or component mixtures to take place with equipment known per se to the person skilled in polyurethane chemistry.

Foaming with a non-aqueous foaming agent, preferably by stirring in or beating in air, is known per se but has particular advantages in this specific case:

The advantageous polyurethane gels according to the invention can thus easily be adjusted to adhere weakly to the skin and adhere well to itself by altering the ratio of polyhydroxyl compound to isocyanate. A reduction in the added amount of isocyanate, based on the polyhydroxyl compound, increases the adhesive force, and an increase in the added amount of isocyanate reduces the adhesive force. This accurate control is possible in a simple manner only when an essentially anhydrous process is carried out. The reason for this is the extremely high water-absorption capacity of the superabsorbers because added water, which must be available for the foaming process, may be and is removed in the process in an uncontrolled manner, so that it becomes much more difficult to adjust the product properties in a targeted manner.

The wound dressings according to the invention with the foam material according to the invention meet all the specified requirements.

Surprisingly, the gel foams according to the invention show the property that they completely lose adhesive properties in the moist milieu of the wound. In addition, it is easily possible to obtain a rapid, intermediate or slow absorption with a high uptake capacity. The foam is moreover weakly or strongly self-adhesive so that it can be adapted satisfactorily to different skin types. It is very important that the absorbed material is virtually not distributed in the area of the wound covering.

The foams can be poured out or spread out to sheet-like structures after a pot life which is advantageously about 0.5–30 minutes. Foam thicknesses of 0.015 mm to 15 cm can be obtained without difficulty in this way. The thickness of material depends in turn on the purpose of use: if a large amount of liquid is to be absorbed per unit area, a correspondingly thick foam material will be spread. If only a small volume of liquid is to be managed per unit area, very thin layers are also sufficient. The "thickness" degree of freedom is necessary because the absorbed liquid is absorbed essentially perpendicular to the wound surface and is not distributed in the surface. Thin applications of composition as far as 10 g/m² can easily be produced in the spreading by using finely ground absorber. However, it is also possible and advantageous to fabricate from the hydrogel foams according to the invention articles which are not sheet-like but markedly space-filling, for example by customary casting processes.

The resulting foams are open-cell foams. It is thus unnecessary to convert them into such by cutting processes.

The hydrogel foams according to the invention can advantageously be applied to the sheet-like backing by processes known per se. One side of the backing is preferably provided with a polyurethane gel foam layer according to the invention.

It is possible according to the invention to use as backing polyurethane sheets because in this way the high flexibility of the polyurethane hydrogel foams is not impeded by the flexible backing material and thus adheres well even in the joint region. Polyurethane sheets of this type are known and commercially obtainable.

The permeabilities to water vapour and permeabilities to air, owing to the open-cell foam structure, of the backing materials used also have the very advantageous effect that the permeabilities for water vapour and air, which are given per se, of the polyurethane hydrogels are retained so that permeability of the pure backing is also achieved. It is therefore also possible in this case to control these properties in a targeted manner by altering, for example, the thickness and nature of the sheet.

The polyurethane gel foams according to the invention have self-adhesive properties, in particular on skin. Very strongly adhesive foam gels adhere pleasantly to the skin and can be pulled off painlessly from normal skin.

By contrast, it is possible to produce for extremely sensitive skin weakly adhesive foams which have sufficient adhesion for it to be possible for them to adhere and easily be fixed. Skin damage has moreover not been observed even with extremely sensitive skin.

The sheets according to the invention can have high flexibility because the foam gel also has these properties. In addition, use is made of the fact that the adhesive gels are well tolerated by skin. Microporous polyurethane sheets are used particularly advantageously because these sheets have special properties. These sheets are preferably impermeable to germs. Their permeability to air and water vapour is variable. Thus, for example, a polyurethane sheet with a thickness of about 35 µm shows a permeability to water vapour and air of about 3500 g/m²/24 hours. The permeability to water vapour of a 25 µm-thick sheet is 6500 g/m²/24 hours. A 50 µm-thick sheet has a permeability to water vapour of 2100 g/m²/24 hours. These types of sheet are moreover all highly flexible so that the high flexibility of the gel foam compositions is shown to good advantage.

A preferred wound dressing according to the invention comprises a polyurethane sheet which is provided with a polyurethane gel foam layer according to the invention. The thickness of this foam gel layer can be 0.1–10 mm, but preferably 0.5–6 mm and particularly preferably 2–4 mm and can thus be suited to the desired capacity. The foam density can be 0.25 to 0.7 g/cm³, preferably 0.3 to 0.65 g/cm³ but in particular 0.45 to 0.6 g/cm³. The liquid uptake takes place very rapidly. The uptake within 90 minutes is preferably 10 to 60 g of water/g of foam gel, particularly preferably 15 to 50 g of water/g of foam gel, but in particular 20 to 40 g of water/g of foam gel. The total uptake capacity is preferably at least 20 g of water/g of foam gel, in particular at least 30 g of water/g of foam gel and particularly preferably at least 40 g of water/g of foam gel. The polyurethane gel foam layer has only weak or very slight self-adhesive properties. Thus, the adhesive force can be up to 0.8 N/cm (measured on steel), preferably 0.06 to 0.6 N/cm (steel), particularly preferably 0.1 to 0.5 N/cm (steel).

Depending on the quality of the raw materials used, preferably 4.7–6.9% by weight, preferably 5.0–6.4% by weight, but in particular 5.4–5.9% by weight of isocyanate are added as crosslinker based on the amount by weight of polyhydroxyl compounds used.

The content by weight of polyhydroxyl compounds based on the total weight of the raw materials used can be between 60 and 80% by weight, preferably between 63 and 77% by weight, but in particular between 65 and 75% by weight.

The content by weight of superabsorber based on the total weight of the raw materials used can be between 20 and 40% by weight, preferably between 23 and 37% by weight, but in particular between 25 and 35% by weight.

This wound dressing is suitable for vary sensitive skin, the skin surface possibly being damaged in some areas and producing a very large amount of discharge. Clear distribution of the discharge beyond the edge of the wound or moist region does not take place. Fixation can take place, for example, additionally using non-adhesive fixing aids.

It is particularly important for use that the material can be removed in one piece. Because of its low adhesive force it is moreover ideally used for seriously damaged skin too.

The material can also be used extremely well on very hairy parts of the body because it can be pulled off essentially without tearing out the hair and can in fact be removed virtually painlessly because, when the material is pulled off, hair is pulled with it only weakly and transiently.

Another preferred wound dressing according to the invention comprises a polyurethane sheet which is provided with a polyurethane gel foam layer according to the invention, whose thickness can be 0.05 to 3 mm, preferably 0.1 to 2 mm, but in particular 0.2 to 1.5 mm. The foam density can be 0.55 to 0.9 g/cm$^3$, preferably 0.6 to 0.85 g/cm$^3$, but in particular 0.65 to 0.8 g/cm$^3$. The liquid uptake likewise takes place rapidly. The uptake within 90 minutes is preferably 5 to 50 g of water/g of foam gel, particularly preferably 7 to 40 g of water/g of foam gel and, in particular 10 to 30 g of water/g of foam gel. The total uptake capacity is preferably at least 15 g of water/g of gel foam, in particular at least 25 g of water/g of foam gel and particularly preferably at least 40 g of water/g of foam gel. The polyurethane gel foam layer has good self-adhesive properties. Thus, the adhesive force can be 0.3 to 2.5 N/cm (measured on steel), preferably 0.5 to 2 N/cm (steel) and particularly preferably 0.6 to 1.7 N/cm. Despite these low adhesive forces measured on steel, the material adheres extremely well to intact skin. The excellent additional properties which have been detailed for the weakly adhesive foam also apply to this more strongly adhesive foam variant.

Depending on the quality of the raw materials used, preferably 4.4–6.4% by weight, preferably 4.6–6.1% by weight, but in particular 5.0–5.6% by weight of isocyanate are added, based on the amount by weight of polyhydroxyl compound used.

The content by weight of polyhydroxyl compounds based on the total weight of the raw materials used can be between 60 and 80% by weight, preferably between 63 and 77% by weight, but in particular between 65 and 75% by weight.

The content by weight of superabsorber based on the total weight of the raw materials used can be between 20 and 40% by weight, preferably between 23 and 37% by weight, but in particular between 25 and 35% by weight.

The wound dressing adheres well in the region of the joints, in particular of the hand, because it is very flexible.

A third preferred wound dressing corresponds to the more strongly self-adhesive dressing described above but preferably has a foam gel layer with a thickness of 0.01 to 1 mm, in particular 0.05 to 0.7 mm, and particularly preferably 0.1 to 0.5 mm. The other features properties correspond to the above statements for the more strongly self-adhesive dressing. The particularly thin and flexible wound dressing is used to prevent the smearing of emerging residual amounts of wound discharge and it thus has, for example, the function of a protective covering. Since this covering is water-impermeable, brief contact with water also causes no problems.

Polyurethane sheets with thicknesses of 10–100 μm are preferred for the three abovementioned wound dressings.

Particularly preferred backings according to the invention for the polyurethane foam gel are flexible polyurethane sheets which are impermeable to water but permeable to water vapour. This particularly applies to the preferred wound dressings described above.

Sheets of this type can be produced, for example, from polyester polyols and/or polyether polyols and/or other polyol compounds with a minimum functionality of 2, which are crosslinked with aliphatic or aromatic polyisocyanates in pure or prepolymerized form and with a minimum functionality of 2.

Sheets of this type preferably have thicknesses of 5–200 μm, preferably 10 to 100 μm, particularly preferably 15 to 70 μm. The values for the permeability to water vapour are preferably 500 to 10,000 g/m$^2$/24 h, preferably 700 to 7000 g/m$^2$/24 h, but in particular 1000 to 5000 g/m$^2$/24 h.

The invention furthermore relates to a process for the production of self-adhesive sheet-like structures based on backing materials coated with polyurethane gel foams. The process is characterized in that the foams defined above or reaction mixtures able to form foam gels are applied to the surface of a backing material, for example by direct processes or reverse processes by casting or knife application, with the surface being, where appropriate, only partially covered by the gel-forming reaction mixture. The layer thickness of the gel foam can be, for example, between 0.01 mm and 150 mm, depending, as described previously, on the desired absorption capacity per unit area.

The sheet-like structures according to the invention can be produced continuously or batchwise. The procedure depends on the given sheet-like structures to be provided with an adhesive layer. A batchwise procedure is often advantageous when backing materials which have already been cut out are available. The continuous procedure is advisable for coating backing materials which are available in continuous form, for example as rolled material. The application of the foam adhesive layer to the backing material can in this case take place directly or by the reverse process. The reaction mixture can also be applied by knife in the said processes before it solidifies due to the reaction.

Although the cohesion of the foams according to the invention is good, it may be advantageous subsequently to treat the foams and sheet-like structures according to the invention by irradiation with gamma rays, which improves the cohesion in the gel layer.

Although it is, as mentioned, possible to control the adhesion properties of the foams according to the invention so that the resulting foams, or the backings coated therewith, can be satisfactorily self-adhesive, they can advantageously be coated on one of the two or else both large areas with a customary self-adhesive composition.

The invention also relates to the use of the polyurethane gel foams according to the invention or of the self-adhesive sheet-like structures, produced therewith, with backings composed of polyurethane sheets as wound dressings.

They can be used, for example, to manage superficial wounds or surgical wounds. They are also suitable as blister plasters. Owing to their padding effect they protect the intact blister, as for example in cases of burns, and cover the wound area when the blister has opened up.

Within the scope of the present application, all amounts and percentage data are, unless otherwise indicated, based on the weight and the complete composition of the formulation.

The following examples are intended to illustrate the invention but without the intention of restricting the invention to these examples.

EXAMPLES

The following reaction components are combined in a commercially available foam mixing head with commercially available metering devices and intimately mixed therein. The composition is then spread on a siliconized paper and covered with another siliconized paper. The composition is then left to react completely at room temperature or at 80° C. The two separating papers are removed to investigate the properties.

Example 1

| | |
|---|---:|
| Polyether polyol (Levagel VP SN 100) | 100 kg |
| Superabsorber (Favor SAB 922-SK) | 39 kg |
| Dibutyltin dilaurate | 0.01 kg |
| Diisocyanate (Desmodur PF) | 6.6 kg |
| Nitrogen | about 300 l |

The result is a weakly adhesive, open-cell foam with a density of 0.45 g/cm$^3$. The material is able to absorb about 25 g of water per gram of its own weight after 90 minutes.

Example 2

| | |
|---|---:|
| Polyether polyol (Levagel VP SN 100) | 100 kg |
| Superabsorber (Favor SAB 922-SK) | 39 kg |
| Dibutyltin dilaurate | 0.01 kg |
| Diisocyanate (Desmodur PF) | 6.6 kg |
| Nitrogen | about 270 l |

The result is a weakly adhesive, open-cell foam with a density of 0.55 g/cm$^3$. The material is able to absorb about 10 g of water per gram of its own weight after 90 minutes.

Example 3

| | |
|---|---:|
| Polyether polyol (Levagel VP SN 100) | 100 kg |
| Superabsorber (Favor SAB 922-SK) | 54 kg |
| Dibutyltin dilaurate | 0.08 kg |
| Diisocyanate (Desmodur PF) | 6.6 kg |
| Nitrogen | about 300 l |

The result is an adhesive, open-cell foam with a density of 0.53 g/cm$^3$. The material has absorbed 115 g of water per gram of its own weight after 90 minutes.

The products of all the examples can also be laminated on one side with a flexible polyester sheet which can be detached only with difficulty, if at all, whereupon the material loses about 40% of its swell-ability (after 90 minutes).

The layer thickness is about 2 mm.

The same results are obtained when other gases such as air or gas mixtures or carbon dioxide are used according to the invention in place of nitrogen in the previous examples.

Materials which can be used in medicine, for example, in particular wound plasters and wound dressings with excellent absorption, are obtained using the foams described above or the backings coated with foam.

Example 4

| | |
|---|---:|
| Polyether polyol (Levagel VP SN 100) | 100 kg |
| Superabsorber (Favor SAB 922-SK) | 39 kg |
| Dibutyltin dilaurate | 0.01 kg |
| Diisocyanate (Desmodur PF) | 6.6 kg |
| Nitrogen so that a density of 0.45 g/cm$^3$ is obtained. | |

About 235–285 l of nitrogen are suitable for this purpose. Variations occur because partial amounts of the nitrogen may be released during production.

The result is a weakly adhesive, self-adhesive, open-cell foam. The material can absorb about 70 g of water per gram of its own weight at a thickness of 3 mm in 90 minutes.

Example 5

| | |
|---|---:|
| Polyether polyol (Levagel VP SN 100) | 100 kg |
| Superabsorber (Favor SAB 922-SK) | 39 kg |
| Dibutyltin dilaurate | 0.01 kg |
| Diisocyanate (Desmodur PF) | 6.6 kg |
| Nitrogen so that a density of 0.5 g/cm$^3$ is obtained. | |

About 200–250 l of nitrogen are suitable for this purpose. Variations occur because partial amounts of the nitrogen may be released during production.

The result is a weakly adhesive, self-adhesive, open-cell foam. The material can absorb about 40 g of water per gram of its own weight after 90 minutes.

Example 6

| | |
|---|---:|
| Polyether polyol (Levagel VP SN 100) | 100 kg |
| Superabsorber (Favor SAB 922-SK) | 39 kg |
| Dibutyltin dilaurate | 0.03 kg |
| Diisocyanate (Desmodur PF) | 5.7 kg |
| Nitrogen so that a density of 0.54 g/cm$^3$ is obtained. | |

About 165–215 l of nitrogen are suitable for this purpose. Variations occur because partial amounts of the nitrogen may be released during production.

The result is a weakly adhesive, open-cell foam which adheres well to itself. The adhesive force on steel was determined to be about 0.4 N/cm. The water uptake after 90 min is about 85 g of water/g of sample. The foam thickness is about 5 mm.

The same results are obtained when other gases such as air or gas mixtures or carbon dioxide are used according to the invention in place of nitrogen in the previous examples.

A foam material which has excellent absorption and is suitable for absorbing any body fluid is obtained using the foams described above and the backings coated with foam. The products are outstandingly suitable for the treatment of deep wounds.

The following reaction components are combined in a commercially available foam mixing head with commercially available metering devices and intimately mixed therein. The composition is then spread on a siliconized paper and covered with a polyurethane sheet. The composition is then left to react completely at 80° C. The separating paper is removed to investigate the properties.

Example 7

| | |
|---|---|
| Polyether polyol (Levagel VP SN 100) | 100 kg |
| Superabsorber (Favor sAB 922-SK) | 38 kg |
| Dibutyltin dilaurate | 0.02 kg |
| Diisocyanate (Desmodur PF) | 5.7 kg |
| Nitrogen so that a density of 0.71 g/cm³ is obtained. | |

About 180–230 l of nitrogen are suitable for this purpose. Variations occur because partial amounts of the nitrogen may be released during production.

The result is a weakly adhesive, open-cell foam. The material can absorb about 35 g of water per gram of its own weight after 90 minutes. The adhesive force on steel is about 0.3 N/cm. The layer thickness is about 3 mm. The liquid is absorbed essentially vertically and virtually not diverted to the side.

The foam can be additionally fixed. The permeability to water vapour is about ⅓ of the original permeability to water vapour of about 6500 g/m²/24 h of polyurethane sheet. The sheet thickness is about 25 μm. The sheet is commercially obtainable (Rexham PU 77).

Example 8

| | |
|---|---|
| Polyether polyol (Levagel VP SN 100) | 100 kg |
| Superabsorber (Favor SAB 922-SK) | 38 kg |
| Dibutyltin dilaurate | 0.02 kg |
| Diisocyanate (Desmodur PF) | 5.3 kg |
| Nitrogen so that a density of 0.71 g/cm³ is obtained. | |

About 80–130 l of nitrogen are suitable for this purpose. Variations occur because partial amounts of the nitrogen may be released during production.

The result is an open-cell foam which adheres well to the skin. The material is able to absorb about 17 g of water per gram of its own weight after 90 minutes. The adhesive force on steel is about 1.1 N/cm. The layer thickness is about 0.75 mm.

The layer thickness of the polyurethane sheet (Rexham PU 77) is about 25 μm and has a permeability to water vapour of about 6500 g/m²/24 h. It is reduced by about 60% by application of the composition.

Example 9

| | |
|---|---|
| Polyether polyol (Levagel VP SN 100) | 100 kg |
| Superabsorber (Favor SAB 922-SK) | 38 kg |
| Dibutyltin dilaurate | 0.02 kg |
| Diisocyanate (Desmodur PF) | 5.3 kg |
| Nitrogen so that a density of 0.66 g/cm³ is obtained. | |

About 100–150 l of nitrogen are suitable for this purpose. Variations occur because partial amounts of the nitrogen may be released during production.

A foam which adheres well to the skin is obtained. The adhesive force on steel is determined to be about 0.6 N/cm. The water uptake is about 13 g of water/g of sample. A polyurethane sheet 50 μm thick with a permeability to water vapour of 2100 g/m²/24 h was used (Rexham 91i). The layer thickness is 0.2 mm.

Corresponding results are obtained when other gases such as air or gas mixtures or carbon dioxide are used according to the invention in place of nitrogen in the previous examples.

Wound plasters and wound dressings with excellent absorption are obtained using the foams described above and the backings coated with foam.

We claim:
1. Self-adhesive, hydrophilic polyurethane gel foams formed by mixing
   1. a polyurethane gel which comprises
      (A) 15–62% by weight, based on the total of (A) and (B) of a covalently crosslinked polyurethane as a matrix and
      (B) 85–38% by weight, based on the total of (A) and (B), of one or more polyhydroxyl compounds which are bound in the matrix by secondary valence forces and have an average molecular weight between 1000 and 12000, and an average OH number between 20 and 112, as liquid dispersant, the dispersant being free of hydroxyl compounds with a molecular weight below 800, and, where appropriate,
      (C) 0–100% by weight, based on the total of (A) and (B), of fillers and/or additives,
   and which is prepared by reacting a mixture of
      a) one or more polyisocyanates
      b) one or more polyhydroxyl compounds with an average molecular weight between 1000 and 12000, and with an average OH number between 20 and 112,
      c) optionally, catalysts or accelerators for the reaction between isocyanate groups and hydroxyl groups and, optionally,
      d) fillers and additives,
   this mixture being free of hydroxyl compounds with a molecular weight below 800, the average functionality of the polyisocyanates ($F_I$) being between 2 and 4, the average functionality of the polyhydroxyl compound ($F_P$) being between 3 and 6, and the isocyanate index (K) being given by the formula

$$K = \frac{300 \pm X}{(F_I \cdot F_P) - 1} + 7$$

in which $X \leq 120$, and the index K has values between 15 and 70,
   2. a water-absorbing material and
   3. a non-aqueous foaming agent, foaming the mixture and curing.

2. Polyurethane gel foam according to claim 1, characterized in that the polyurethane gel contains (A) 20–57% by weight, based on the total of (A) and (B), of the covalently crosslinked polyurethane and (B) 80–43% by weight, based on the total of (A) and (B), of the polyhydroxyl compounds of the liquid dispersant.

3. Polyurethane gel foam according to claim 1, characterized in that the polyurethane gel contains (A) 25–47% by weight of the covalently crosslinked polyurethane and (B) 75–53% by weight of the polyhydroxyl compounds of the liquid dispersant.

4. Polyurethane gel foam according to claim 1, characterized in that the polyhydroxyl compounds are polyether polyols.

5. Polyurethane gel foams according to claim 1, characterized in that the diisocyanates are chosen from the group of unmodified aromatic or aliphatic diisocyanates, for example 4,4'-diisocyanatodiphenylmethane, and of modified products formed by prepolymerization with polyols or polyether polyols, for example of 4,4'-diisocyanatodiphenylmethane liquefied by prepolymerization with tripropylene glycol.

6. Polyurethane gel foams according to claim 1, characterized in that the accelerators are chosen from the group consisting of organic acids, organotin compounds, including their salts with organic and inorganic acids, iron salts of higher fatty acids, amines, tertiary amines.

7. Polyurethane gel foam according to claim 1, characterized in that the water-absorbing material is a superabsorber.

8. Polyurethane gel foam according to claim 1, characterized in that the non-aqueous foaming agents are nitrogen, air or carbon dioxide or mixtures of these gases.

9. Polyurethane gel foams according to claim 1, formed by mixing

| | |
|---|---|
| 20 | 95% by weight of polyhydroxyl compound |
| 1 | 60% by weight of polyisocyanate |
| 5 | 60% by weight of [superabsorber] a water absorbing material |
| 0.0001 | 10% by weight of accelerator | and the non-aqueous foaming agent in an amount which affords densities of 0.15 to 1.1 g/cm³, foaming the mixture and curing.

10. Polyurethane gel foams according to claim 1, formed by mixing

| | |
|---|---|
| 50 | 70% by weight of polyhydroxyl compound |
| 2 | 25% by weight of polyisocyanate |
| 5 | 40% by weight of [superabsorber] a water absorbing material |
| 0.001 | 1% by weight of accelerator | and the non-aqueous foaming agent in an amount which affords densities of 0.3 to 1.0 g/cm³, foaming the mixture and curing.

11. Process for the production of the polyurethane foams according to claim 1, characterized in that
 1. the components (A), (B) and (C) of the polyurethane gel
 2. a water-absorbing material and
 3. a non-aqueous foaming agent are combined and mixed together and foamed.

12. Self-adhesive sheet structures consisting of a sheet backing to which is applied a polyurethane foam gel according to claim 1.

13. Process for the production of the self-adhesive sheet structures of claim 12, wherein said mixture is applied to said backing, and then foamed and cured on said backing.

14. An adhesive plaster, wound plaster, wound dressing, bandage or support, protective material or padding material comprising the self-adhesive, hydrophilic polyurethane gel foam of claim 1.

15. Hydrophilic polyurethane gel foams formed by mixing
 1. a polyurethane gel which comprises
  (A) 35–62% by weight, based on the total of (A) and (B) of a covalently crosslinked polyurethane as a matrix and
  (B) 65–38% by weight, based on the total of (A) and (B), of one or more polyhydroxyl compounds which are bound in the matrix by secondary valence forces and have an average molecular weight between 1000 and 12000, and an average OH number between 20 and 112, as liquid dispersant, the dispersant being free of hydroxyl compounds with a molecular weight below 800, and, optionally,
  (C) 0–100% by weight, based on the total of (A) and (B), of fillers and/or additives,
 and which is prepared by reacting a mixture of
  a) one or more polyisocyanates
  b) one or more polyhydroxyl compounds with an average molecular weight between 1000 and 12000, and with an average OH number between 20 and 112,
  c) where appropriate catalysts or accelerators for the reaction between isocyanate groups and hydroxyl groups and, optionally,
  d) fillers and additives,
 this mixture being free of hydroxyl compounds with a molecular weight below 800, the average functionality of the polyisocyanates ($F_I$) being between 2 and 4, the average functionality of the polyhydroxyl compound ($F_P$) being between 3 and 6, and the isocyanate index (K) being given by the formula $$K = \frac{300 \pm X}{(F_I \cdot F_P) - 1} + 7$$

in which $X \leq 120$, and the index K has values between 15 and 70, where the stated averages of molecular weight and OH number are to be understood as number averages,
 2. a water-absorbing material and
 3. a non-aqueous foaming agent, foaming the mixture and curing.

16. Polyurethane gel foam according to claim 15, characterized in that the polyurethane gel contains
 (A) 42–60% by weight, based on the total of (A) and (B), of the covalently cross-linked polyurethane and
 (B) 58–40% by weight, based on the total of (A) and (B), of the polyhydroxyl compounds of the liquid dispersant.

17. Polyurethane gel foam according to claim 15, characterized in that the polyurethane gel contains
 (A) 49–57% by weight, based on the total of (A) and (B), of the covalently cross-linked polyurethane and
 (B) 51–43% by weight, based on the total of (A) and (B), of the polyhydroxyl compounds of the liquid dispersant.

18. Polyurethane gel foam according to claim 15, characterized in that the polyhydroxyl compounds are polyether polyols.

19. Polyurethane gel foams according to claim 15, characterized in that the diisocyanates are chosen from the group of unmodified aromatic or aliphatic diisocyanates, and of modified products formed by prepolymerization with polyols or polyether polyols.

20. Polyurethane gel foams according to claim 15, characterized in that the accelerators are chosen from the group consisting of organic acids, organotin compounds, including their salts with organic and inorganic acids, iron salts of higher fatty acids, amines, tertiary amines.

21. Polyurethane gel foam according to claim 15, characterized in that the water-absorbing material is a superabsorber.

22. Polyurethane gel foam according to claim 15, characterized in that the non-aqueous foaming agents are nitrogen, air or carbon dioxide or mixtures of these gases.

23. Polyurethane gel foams according to claim 15, prepared by mixing

| | |
|---|---|
| 40 | 95% by weight of polyhydroxyl compound |
| 1 | 20% by weight of polyisocyanate |
| 1 | 60% by weight of a water absorbing material |
| 0.0001 | 10% by weight of accelerator | and the non-aqueous foaming agent in an amount which affords densities of 0.45 to 0.6 g/cm³, foaming the mixture and curing.

24. Polyurethane gel foams according to claim 15, formed by mixing

| | |
|---|---|
| 55 | 85% by weight of polyhydroxyl compound |
| 2 | 10% by weight of polyisocyanate |
| 20 | 40% by weight of [superabsorber] a water absorbing material |
| 0.001 | 1% by weight of acceletator | and the non-aqueous foaming agent in an amount which affords densities of 0.15 to 1.1 g/cm³, foaming the mixture and curing.

25. Process for the production of the polyurethane foams according to claim 15, characterized in that
  1. the components (A), (B) and (C) of the polyurethane gel
  2. a water-absorbing material and
  3. a non-aqueous foaming agent are combined and mixed together and foamed.

26. Polyurethane gel foams according to claim 15, characterized in that the amount by weight of the water-absorbing material is 24 to 67% by weight of the weight of the polyhydroxyl compounds.

27. Polyurethane gel foams according to claim 15, characterized in that the amount by weight of isocyanate is 4.7 to 6.9% by weight of the weight of the polyhydroxyl compounds.

28. Polyurethane gel foam according to claim 15, characterized in that the content by weight of polyhydroxyl compounds is 60–80% by weight based on the total weight.

29. Wound dressings comprising a polyurethane sheet as backing and hydrophilic polyurethane gel foams applied thereto, which are formed by mixing
  1. a polyurethane gel which comprises
    (A) 25–62% by weight, based on the total of (A) and (B) of a covalently crosslinked polyurethane as a matrix and
    (B) 75–38% by weight, based on the total of (A) and (B), of one or more polyhydroxyl compounds which are bound in the matrix by secondary valence forces and have an average molecular weight between 1000 and 12000, and an average OH number between 20 and 112, as liquid dispersant, the dispersant being free of hydroxyl compounds with a molecular weight below 800, and, optionally,
    (C) 0–100% by weight, based on the total of (A) and (B), of fillers and/or additives,
  and which is prepared by reacting a mixture of
    a) one or more polyisocyanates
    b) one or more polyhydroxyl compounds with an average molecular weight between 1000 and 12000, and with an average OH number between 20 and 112,
    c) where appropriate catalysts or accelerators for the reaction between isocyanate groups and hydroxyl groups and, optionally,
    d) fillers and additives,
  this mixture being free of hydroxyl compounds with a molecular weight below 800, the average functionality of the polyisocyanates ($F_I$) being between 2 and 4, the average functionality of the polyhydroxyl compound ($F_P$) being between 3 and 6, and the isocyanate index (K) being given by the formula $$K = \frac{300 \pm X}{(F_I \cdot F_P) - 1} + 7$$

in which $X \leq 120$, and the index K has values between 15 and 70, where the stated averages of molecular weight and OH number are to be understood as number averages,
  2. a water-absorbing material and
  3. a non-aqueous foaming agent, foaming the mixture and curing.

30. Wound dressing according to claim 29, characterized in that the polyurethane gel contains
  (A) 30–60% by weight, based on the total of (A) and (B), of the covalently crosslinked polyurethane and
  (B) 70–40% by weight, based on the total of (A) and (B), of the polyhydroxyl compounds as liquid dispersant.

31. Wound dressing according to claim 29, characterized in that the polyurethane gel contains
  (A) 40–57% by weight, based on the total of (A) and (B), of the covalently crosslinked polyurethane and
  (B) 30–43% by weight, based on the total of (A) and (B), of the polyhydroxyl compounds as liquid dispersant.

32. Wound dressing according to claim 29, characterized in that the polyhydroxyl compounds are polyether polyols.

33. Wound dressing according to claim 29, characterized in that the diisocyanates are chosen from the group of unmodified aromatic or aliphatic diisocyanates, for example 4,4'-diisocyanatodiphenylmethane, and of modified products formed by prepolymerization with polyols or polyether polyols, for example of 4,4'-diisocyanatodiphenylmethane liquified by prepolymerization with tripropylene glycol.

34. Wound dressing according to claim 29, characterized in that the accelerators are chosen from the groups consisting of
  organic acids,
  organotin compounds, including their salts with organic and inorganic acids,
  iron salts of higher fatty acids,
  amines,
  tertiary amines.

35. Wound dressing according to claim 29, characterized in that the water-absorbing material is a superabsorber.

36. Wound dressing according to claim 29, characterized in that the non-aqueous foaming agents are nitrogen, air or carbon dioxide or mixtures of these gases.

37. Wound dressing according to claim 29, characterized in that the polyurethane gel foam is formed by mixing

| | |
|---|---|
| 20 | 95% by weight of polyhydroxyl compound |
| 1 | 30% by weight of polyisocyanate |
| 1 | 60% by weight of [superabsorber] a water absorbing material |
| 0.0001 | 10% by weight of accelerator | the non-aqueous foaming agent in an amount which affords densities of 0.15 to 1.1 g/cm³, foaming the mixture and curing.

38. Wound dressing according to claim 29, characterized in that the polyurethane gel foam is formed by mixing

| 55    | 85% by weight of polyhydroxyl compound                     |
|-------|------------------------------------------------------------|
| 2     | 15% by weight of polyisocyanate                            |
| 5     | 40% by weight of [superabsorber] a water absorbing material |
| 0.001 | 1% by weight of accelerator                                | and the non-aqueous foaming agent in an amount which affords densities of 0.3 to 1.0 g/cm$^3$, foaming the mixture and curing.

39. Process for the production of the wound dressings according to claim 29, characterized in that
1. the components (A), (B) and (C) of the polyurethane gel
2. a water-absorbing material and
3. a non-aqueous foaming agent are combined and mixed together and foamed and applied to a polyurethane sheet.

40. Wound dressing according to claim 29, characterized in that the amount by weight of the water-absorbing material is 24–67% by weight, based on the weight of the polyhydroxyl compound.

41. Wound dressings according to claim 29, characterized in that the foam density is 0.3 to 0.65 g/cm$^3$.

42. Wound dressing according to claim 29, characterized in that the thickness of the foam gel layer is 0.1–10 mm, the foam density is 0.25 to 0.7 g/cm$^3$, the water uptake in 90 min is 10–60 g of water/g of foam gel, the total uptake capacity is at least 20 g of water/g of foam gel, and the adhesive force is up to 0.8 N/cm (measured on steel).

43. Wound dressing according to claim 29, characterized in that the thickness of the foam gel layer is 0.05–3 mm, the foam density is 0.55 to 0.9 g/cm$^3$, the water uptake in 90 min is 5–50 g of water/g of foam gel, the total uptake capacity is at least 15 g of water/g of foam gel, and the adhesive force is up to 0.3–2.5 N/cm (measured on steel).

44. Wound dressing according to claim 29, characterized in that the thickness of the foam gel layer is 0.01–1 mm, the foam density is 0.55 to 0.9 g/cm$^3$, the water uptake in 90 min is 5–50 g of water/g of foam gel, the total uptake capacity is at least 15 g of water/g of foam gel, and the adhesive force is up to 0.3–2.5 N/cm (measured on steel).

45. Wound dressing according to claim 29, characterized in that one side of a polyurethane sheet is provided with a layer of a polyurethane gel foam.

46. An adhesive plaster, wound plaster or blister plaster comprising the wound dressing of claim 29.

* * * * *

UNITED STATES PATENT AND TRADEMARK OFFICE
CERTIFICATE OF CORRECTION

PATENT NO. : 5,844,013

DATED : December 1, 1998

INVENTOR(S) : Jochen Kenndoff, et al.

It is certified that error appears in the above-identified patent and that said Letters Patent is hereby corrected as shown below:

| | |
|---|---|
| Col. 25, Line 19 | After "60% by weight of" delete "[superabsorber]" |
| Col. 25, Line 30 | After "40% by weight of" delete "[superabsorber]" |
| Col. 27, Line 18 | After "40% by weight of" delete "[superabsorber]" |

Signed and Sealed this

Second Day of November, 1999

Attest:

Q. TODD DICKINSON

Attesting Officer

Acting Commissioner of Patents and Trademarks